United States Patent
Chianese

[19]

[11] Patent Number: 5,804,141
[45] Date of Patent: Sep. 8, 1998

[54] REAGENT STRIP SLIDE TREATING APPARATUS

[76] Inventor: David Chianese, 41 St. Paul Rd., Ardmore, Pa. 19003

[21] Appl. No.: 720,979

[22] Filed: Oct. 15, 1996

[51] Int. Cl.⁶ .................................................. G01N 35/10
[52] U.S. Cl. .............................. 422/63; 422/81; 422/109; 422/103; 422/104; 436/43; 436/46; 436/165; 436/174; 436/180
[58] Field of Search ................................ 422/58, 61, 63, 422/68.1, 73, 81, 99, 100, 102, 103, 104; 436/43, 46, 52, 164, 165, 174, 179, 180

[56] References Cited

U.S. PATENT DOCUMENTS

| | | | |
|---|---|---|---|
| Re. 29,725 | 8/1978 | Johnson et al. | 422/65 |
| 2,932,385 | 4/1960 | Bollmeier et al. | 206/47 |
| 3,754,863 | 8/1973 | Reunanen | 23/230 R |
| 3,764,215 | 10/1973 | Wallach | 356/36 |
| 3,799,742 | 3/1974 | Coleman | 23/253 R |
| 3,837,795 | 9/1974 | Becker et al. | 8/3 |
| 3,951,605 | 4/1976 | Natelson | 23/253 R |
| 4,038,030 | 7/1977 | Albright et al. | 422/65 |
| 4,065,263 | 12/1977 | Woodbridge, III | 23/253 TP |
| 4,199,613 | 4/1980 | Johnson | 427/2 |
| 4,358,470 | 11/1982 | Rasmussen | 427/4 |
| 4,458,811 | 7/1984 | Wilkinson | 206/219 |
| 4,673,657 | 6/1987 | Christian | 436/501 |
| 4,690,801 | 9/1987 | Anderson | 422/68 |
| 4,731,335 | 3/1988 | Brigati | 436/180 |
| 4,731,337 | 3/1988 | Luotola et al. | 436/526 |
| 4,743,536 | 5/1988 | Evanega et al. | 435/7 |
| 4,777,020 | 10/1988 | Brigati | 422/99 |
| 4,801,431 | 1/1989 | Cuomo et al. | 422/104 |
| 4,837,159 | 6/1989 | Yamada | 436/45 |
| 4,837,160 | 6/1989 | Meserol et al. | 436/45 |
| 4,847,208 | 7/1989 | Bogen | 436/174 |
| 4,965,047 | 10/1990 | Hammond | 422/58 |
| 5,009,185 | 4/1991 | Stokes et al. | 118/52 |
| 5,023,187 | 6/1991 | Koebler et al. | 436/180 |
| 5,073,504 | 12/1991 | Bogen | 436/174 |
| 5,180,606 | 1/1993 | Stokes et al. | 427/2 |
| 5,217,905 | 6/1993 | Marchand et al. | 436/518 |
| 5,231,029 | 7/1993 | Wootton et al. | 435/289 |
| 5,288,463 | 2/1994 | Chemelli | 422/58 |
| 5,290,518 | 3/1994 | Johnston | 422/58 |
| 5,322,771 | 6/1994 | Rybski et al. | 435/7.2 |
| 5,364,591 | 11/1994 | Green et al. | 422/58 |
| 5,374,395 | 12/1994 | Robinson et al. | 422/64 |
| 5,418,138 | 5/1995 | Miller et al. | 435/7.2 |
| 5,425,918 | 6/1995 | Healey et al. | 422/64 |

*Primary Examiner*—Long V. Le
*Attorney, Agent, or Firm*—Michael F. Petock, Esq.

[57] ABSTRACT

A reagent strip slide treating apparatus includes a reagent strip comprised of a plurality of chambers. A reagent passageway on the strip connects to each of the chambers and connects to a common passageway. The chambers are arranged at variable predetermined distances along the strip. A double slide is provided which is comprised of a first and a second slide spaced apart by a predetermined distance and adapted to have therebetween biological material to be treated sequentially by a plurality of reagents. A tube connects the common passageway of the reagent strip to the space between the space slides. The capsules containing reagents are provided within the chambers on the strip. The capsules are provided with thin walls which are adapted to burst upon the application of pressure. A press moving at a constant speed is provided to press the reagent strip and capsules in the chambers causing the capsules to burst. The spacing between the chambers determines the timing of the application of the reagents. The strip may preferably be straight, although it may be curved such as an arc or a roller may be mounted on a radial arm.

11 Claims, 3 Drawing Sheets

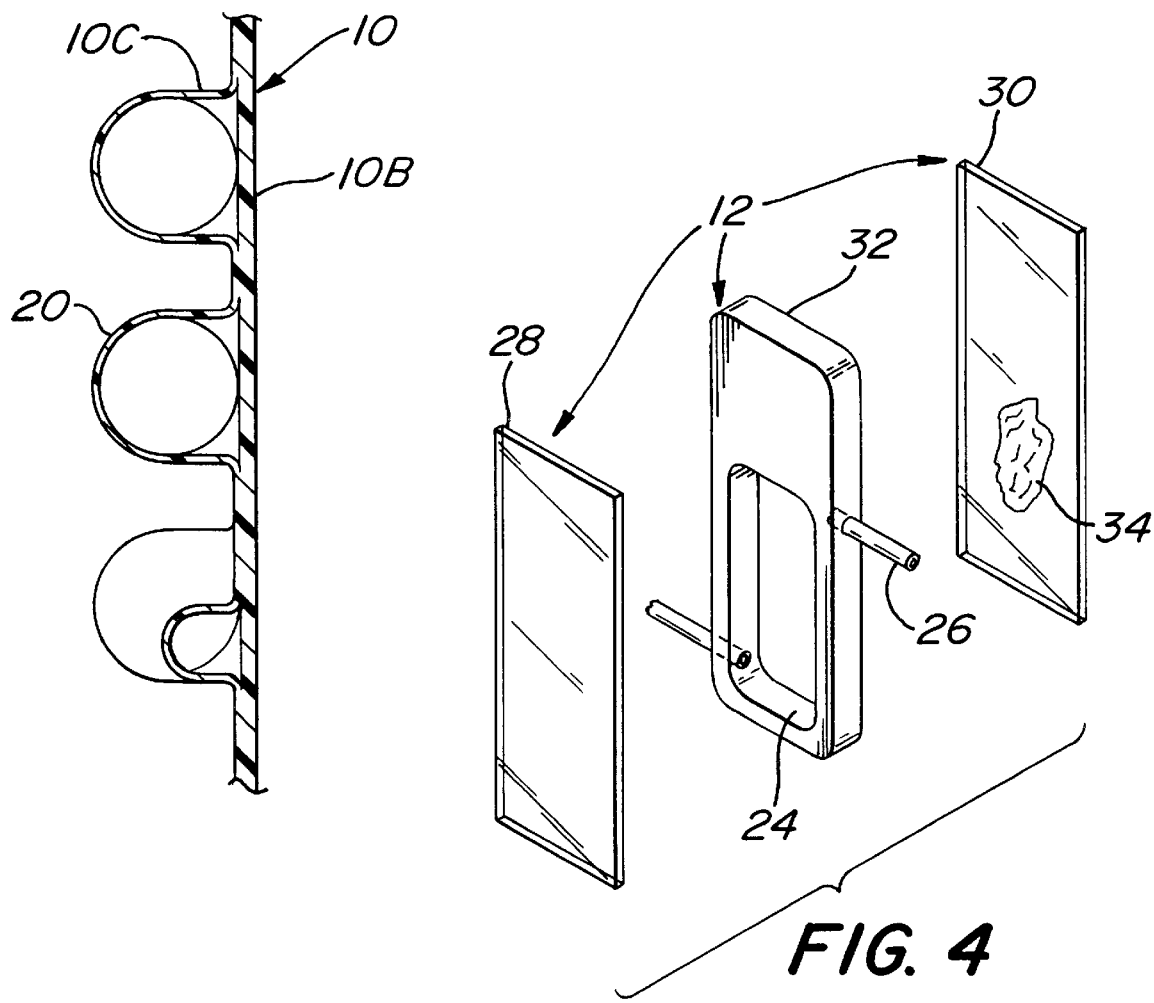
FIG. 2
FIG. 4
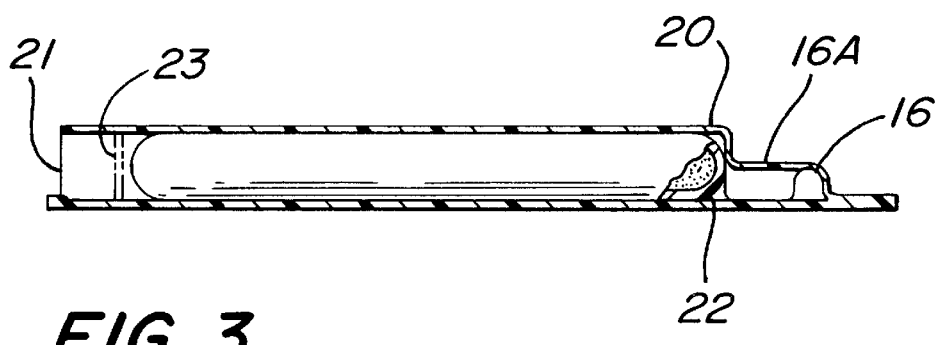
FIG. 3

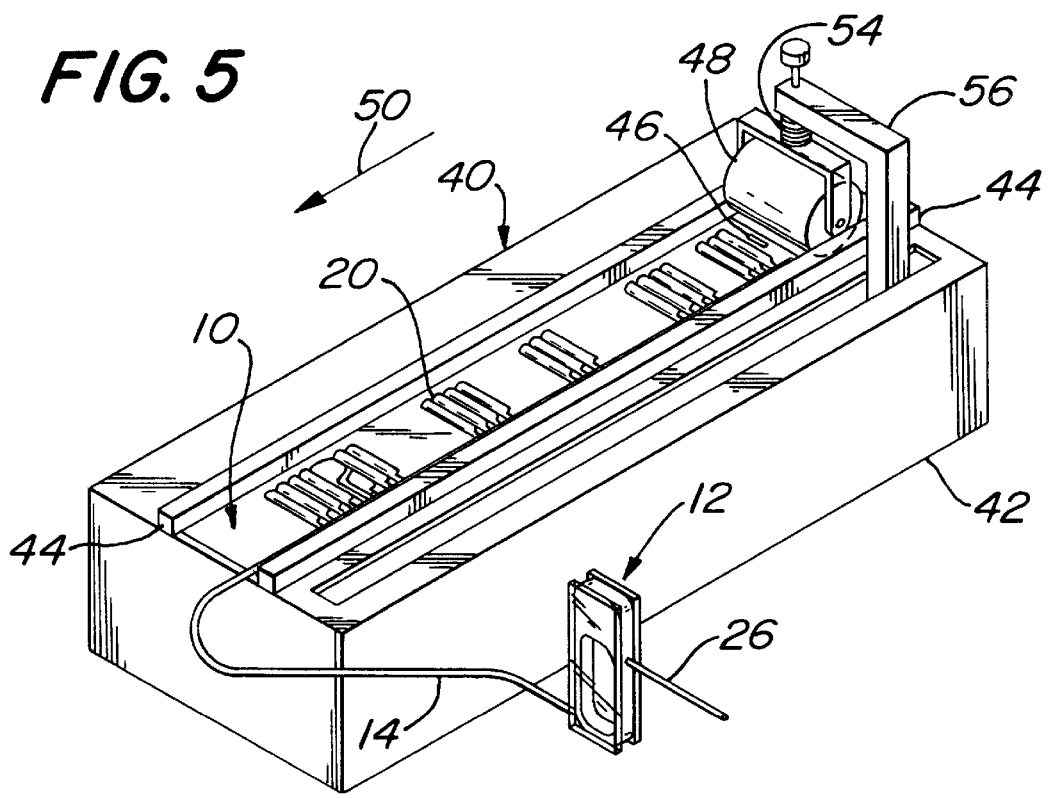
FIG. 5
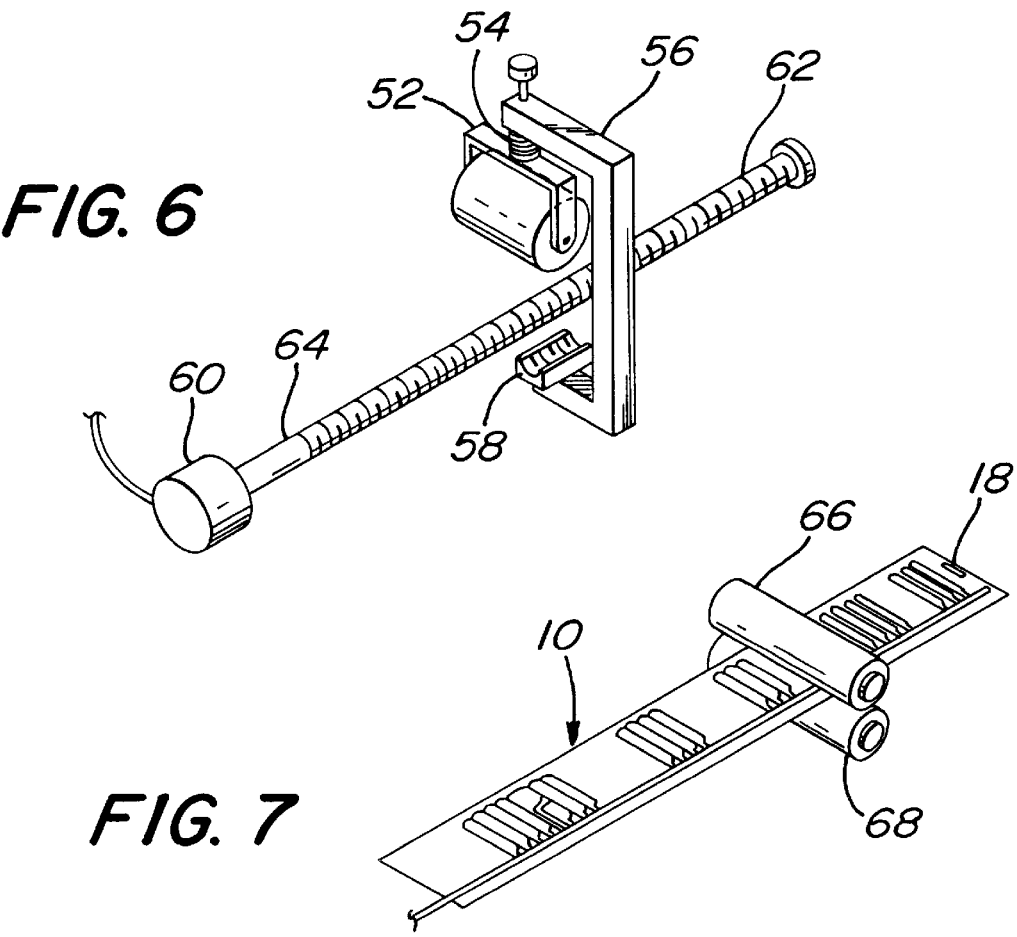
FIG. 6
FIG. 7

REAGENT STRIP SLIDE TREATING APPARATUS

FIELD OF THE INVENTION

The present invention relates to apparatus for staining or treating biological material. More particularly, the present invention relates to an apparatus for automatically sequentially providing reagents to biological material which is to be microscopically analyzed.

BACKGROUND OF THE INVENTION

Currently, microscope slides prepared with blood films, cytologic material, and histologic thin sections are used to render clinical diagnoses in medical disease states. In order to visualize the biological material on the slides, dyes, chemical enzymes and antibody and chromogen substrate systems are used to identify cellular properties which are used to characterize a disease process.

Traditionally, dyes such as hematoxylin and eosin are used for routine staining of histologic samples. This staining is generally accomplished by manual dipping of racks of slides into baths containing reagents or stains.

As the complexity of histochemical methods increased, many long and multi-step procedures were developed to utilize dye and enzymatic reactions specific for selected biologic properties of individual diseases. This information augmented the traditional method of the analysis of cellular morphology and architecture for a disease diagnosis, and allowed a more precise and accurate characterization. Again, these procedures were performed by immersing slides into baths of reagents. As the complexity of the number and type of reagents used increased, the required skill level of the technician also increased. Many procedures began to require a highly trained individual to assure proper reaction times and to assure the proper chemical properties of the reagents used. With this added complexity came limitations in the type and number of these special stains that a technician could perform in a given period of time.

With the advent of immunohistochemical methods, which utilize specific antibody enzyme and substrate preparations, to label specific and diagnostic antigens on cell structures, the complexity of microscope slide based assays increased dramatically. The number of steps involved, the incubation times of the reactions and washes, as well as the price of the reagents, mandated that automated methods be developed to perform these procedures. Bath staining or incubation proved too expensive for the antibody reagents. In addition, many different antibody preparations with unique specificities were being used in parallel on the same series of slides, at the same time. To adapt to these limitations, most of these reactions were performed with the slides laying flat, on racks, in some sort of humidification chamber. This allowed incubation with a small amount of reagent (50–200 microliter) per slide. However, with this technique came a significant amount of slide handling and the risk of reagents drying on the slides, resulting in nonspecific staining. Attempts to deal with these handling problems were addressed by Brigati and Johnson (see U.S. Pat. No. 4,731,335; 5,023,187; 4,777,020; 4,801,431 and 4,199,613) with utilization of a capillary gap, formed between two slides, placed face to face. This configuration could be used to draw up reagents from a surface, incubate in a closed chamber and wick the reagents into an absorbent pad. The reagent volumes were small, and platforms were created to handle large numbers of slides in parallel. The demands of capillary action required strict tolerances for slide spacing shims, tissue section thickness and buffer formulation to assure that the capillary gap would draw the correct amount of reagent to the proper height. In addition to these problems, a large instrument with multiple reagent trays was necessary to deliver the reagents for the capillary gap procedure.

Other instruments were developed to perform immunohistochemistry procedures by automating the reagent addition to slides held in a rack. These instruments relied on a pipette or nozzle to apply reagents and a series of pumps and valves under microprocessor control. The level of instrument complexity increased and the potential for slide drying was still present. In addition, these instruments were limited in number and in the diversity of reactions that could be performed at the same time.

SUMMARY OF THE INVENTION

The present invention provides the advantage of providing a relatively simple structure which does not require a computer controlled system to stain or otherwise treat material on a microscope slide, particularly where the reagent or staining material needs to be applied sequentially in a predetermined sequence and with predetermined time intervals.

Another advantage of the present invention is that complex methods of histochemistry and immunochemistry which require precise delivery of a sequence of reagents, with fixed incubation times may be easily and quickly provided in the laboratory without consuming large amounts of skilled technical time.

Another advantage of the present invention is that a number of assays or preparations that can be performed in a given period of time may be increased.

Another advantage of the present invention is that since the reagents are pre-prepared, and sealed in a strip, the reagent manufacturer can control how the reagents are handled. Another advantage of the present invention is that reproducibility and quality control in histochemistry and immunochemistry may be improved.

Another advantage of the present invention is that specific tests and reagent sequences may be pre-provided at a predictable and reduced cost per laboratory test.

Another advantage of the present invention is that the reagents are prepackaged in a sealed unit, which reagents are supplied to the material on the slide without the need for human handling or contact.

Briefly and basically, the present invention comprises a reagent strip slide treating apparatus which includes a reagent strip. The reagent strip is comprised of a plurality of chambers. A reagent passageway connects to each of the chambers and connects to a common passageway. The plurality of chambers are arranged at variable predetermined distances along the strip. A double slide is provided which is comprised of a first and a second slide spaced apart by a predetermined distance and adapted to have therebetween biological material to be treated sequentially by a plurality of reagents. A tube connects the common passageway of the reagent strip to the space between the spaced slides. A plurality of capsules containing reagents are provided within the chambers. The capsules are provided with thin walls which are adapted to burst upon the application of pressure. A press structure is provided for providing pressure to the reagent strip and the capsules in the chambers. The pressure is applied at a uniform rate of speed along a predetermined length of the strip. The strip in a preferred embodiment is straight, but it may be curved or another suitable shape. For example, the strip may be formed in an arc such as a 45 degree arc or a semi-circle, with a roller rotating on a radial arm along the arc. The spacing between the slides is selected to be greater than that which would draw reagent into the space between the slides by capillary action. The slide is preferably placed in a substantially vertical direction requiring positive pressure against the force of gravity, thereby providing uniform staining with the reagents.

BRIEF DESCRIPTION OF THE DRAWINGS

For the purpose of illustrating the invention, there are shown in the drawings forms which are presently preferred; it being understood, however, that this invention is not limited to the precise arrangements and instrumentalities shown.

FIG. 2 is a cross sectional view taken along line 2—2 of FIG. 1.

FIG. 3 is a cross sectional view taken along line 3—3 of FIG. 1.

FIG. 4 is an exploded view of a slide utilized in connection with the present invention.

FIG. 5 is a view in perspective of a reagent strip slide treating apparatus including an apparatus for providing pressure to the reagent strip at a uniform rate of speed.

FIG. 6 is a view in perspective of a drive means for the pressing apparatus of FIG. 5.

FIG. 7 is an alternate embodiment of a structure for providing pressure to a reagent strip at a uniform rate of speed.

DETAILED DESCRIPTION OF THE PREFERRED EMBODIMENTS

Figure 1:
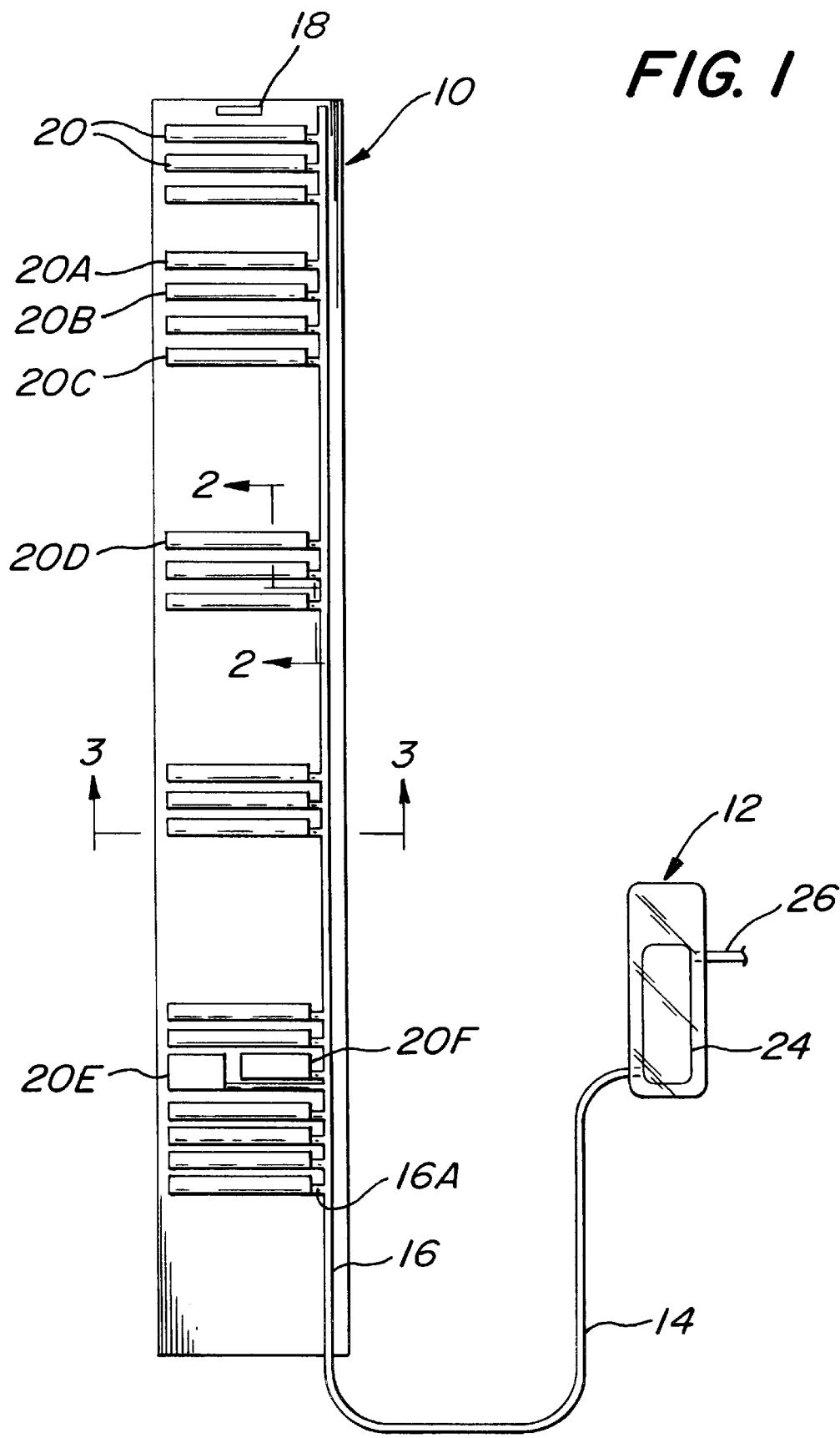
FIG. 1 is an elevation view of a reagent strip slide treating apparatus, including the reagent strip and the slide, in accordance with the present invention.

Referring now to the drawings in detail, wherein like numerals indicate like elements, there is shown in FIG. 1 a reagent strip 10, a double slide 12 and a tube 14 connecting a common passage way 16 of the reagent strip 10 with the double slide 12. Opening 18 in reagent strip 10 may be utilized for indexing or positioning of the reagent strip on a pressing device to easily and conveniently coordinate a starting position or starting time. However, it is understood that various other types of indexing device may be used including notches along the side or the index opening 18 may be placed at various other places along the reagent strip.

Referring now more particularly to FIGS. 1, 2 and 3 taken together, reagent strip 10 is provided with a plurality of chambers 20. Each chamber along its right side is connected to common passageway 16. Each chamber 20 is adapted to receive a capsule 22 containing a reagent. The chambers 20 may be selectively positioned along strip 10 such that a pressure sequentially applied along the strip will result in the bursting of the capsules and the emptying of the reagent into the common passageway in a predetermined sequence and timing.

The capsules 22 may be inserted into chamber 20 from the left side in FIG. 1. The left side of chamber 20 may then be sealed. However, the reagent strip may be manufactured by various other suitable processes wherein a reagent is placed within capsules along the length of the strip, in such a sequence and arrangement that the reagent is squeezed out of the capsule and into the common passageway and delivered to a space 24 between the slides of double slide 12. The reagent is delivered from common passageway 16 via tube 14 to space 24. Any excess reagent is removed through outlet 26.

A more detailed view of the structure of double slide 12 is illustrated in FIG. 4 wherein double slide 12 is comprised of a first slide 28, a second slide 30 and a spacer 32 having space 24 where the reagents for staining material on one of the slides 28 or 30 is provided. The material to be stained or otherwise treated is shown at 34 on slide 30 in FIG. 4 for convenience. However, it is understood that this biological material could be on either slide 28 or 30.

The reagent strip slide treating apparatus of the present invention may be utilized in connection with the treating of various biological materials on a slide to be viewed under a microscope. These treating processes which includes staining of biological material often unusually require the application of various reagents in a predetermined sequence for predetermined periods of time, that is predetermined intervals between the application of one reagent and the next reagent, wash or the like. The term reagent herein is defined to include any type of fluid material that may be applied to the biological material on the slide, including buffers, washes, water washes and any other material applied in the process of treating the biological material on the slide to be viewed under the microscope. One example of a standard treating protocol is the following standard immunohistochemistry Biotin-Strepavidin Reagent Protocol:

1. buffer 5 min.;
2. block reagent 10 min.;
3. wash buffer 5 min.;
4. wash buffer 5 min.;
5. primary antibody 30 min.;
6. wash buffer 5 min.;
7. wash buffer 5 min.;
8. biotinylated secondary 30 min.;
9. wash buffer 5 min.;
10. wash buffer 5 min.;
11. avidin-peroxidase 30 min.;
12. wash buffer 5 min.;
13. wash buffer 5 min.;
14a. peroxide substrate;
14b. diaminobenzidine chromogen 5 min.;
15. water wash 5 min.;
16. hematoxylin counterstain 5 min.;
17. bluing agent 5 min.; and
18. water wash until end of cycle.

This particular protocol is not illustrated in the drawings, but is merely submitted as an example of the types of protocols that might be carried out using the reagent strip slide treating apparatus of the present invention.

Any suitable means of sequentially applying pressure to reagent strip 10 at a constant rate of speed to compress or squeeze the chambers 20 with the capsules 22 may be utilized in carrying out the present invention. Specific examples of such structure are shown in FIGS. 5, 6 and 7 to be described hereinafter. As illustrated in FIGS. 5 through 7, preferably, a rolling device, rolling at a constant speed is a presently preferred form of applying the sequential pressure to compress or squeeze the chambers 20 and the enclosed capsules 22. However, it is understood that other suitable means for applying pressure may be utilized including a process wherein the strip is fed at a constant rate of motion into a device which has a reciprocating compressing platen. Other means suitable for compressing the chambers at a uniform rate of speed will be apparent to those skilled in the art including a means for feeding the strip into a narrow slit or opening at a constant rate of speed.

The spacing and arrangement of the chambers 20 will vary depending upon the particular treating or staining protocol to be utilized in the particular case. However, referring to FIG. 1, as an illustration of the concept the reagent strip 10 may be approximately 450 mm long with a spacing of 10 mm between chambers 20 A and 20 B. The spacing between chambers 20 C and 20 D may be 60 mm. Chambers 20 E and F illustrate a protocol step where two reagents are to be applied simultaneously. This commonly occurs where the two reagents cannot be premixed in advance, but have to be mixed at the time of application. An example of such a step is illustrated above in steps 14a and 14b in the Biotin-Strepavidin Reagent Protocol.

One suitable procedure for manufacturing the reagent strips 10 is to have the reagents sealed within capsules 22 which capsules are then inserted into chambers 20 via the left hand side of reagent strip 10 of FIG. 1, a cross sectional view of which is shown in FIG. 3. The reagent capsule 22 would be inserted through opening 21. Once all of the capsules 22 are inserted into chambers 20, opening 21 is sealed by a suitable process such as heat sealing or ultrasonic bonding and is shown in dotted outline form at 23.

In running the protocol for treating the biological material on a slide, when one of the chambers 20 with an enclosed capsule 22 is compressed, the capsule bursts and the reagent flows into common passageway 16, through the common passageway connection 16 A. Reagents 20 are not mixed with subsequent reagents due to the fact that each chamber contains a sealed capsule until compressed. The reagent flows through common passageway 16 and tubing 14 to the space 24 to stain or otherwise treat the biological material 34 on one of the slides. Tube 14 is referred to as a tube for convenience, but it is understood that it may be any suitable means for carrying the reagents from the common passageway 16 to the space 24 between the double slides.

Reagent strips 10 may preferably be molded from polyethylene, but it is understood that any suitable material may be utilized. Reagent strip 10 is preferably molded to provide a relatively thick base 10B and a thinner chamber portion 10C. as may be best seen in FIG. 2. However, it is understood that other suitable materials and arrangements may be utilized to create the compressible chambers 20.

In summary, inside each reagent chamber 22 is a sealed thin walled sealed tube or capsule 22 containing a specific reagent. As a roller or other pressing means advances, which creates pressure and breaks a capsule 22, the reagent is released down the common passageway 16 which is molded into the reagent strip 10, to react with the cellular or other biological material present on the microscope slide. The advance or down strip reagent capsules 22 are sealed to prevent unwanted mixing of reagents. In addition, the sealed capsules prevent the reagents from leaking into the advance chambers, and insures that all of the reagent is delivered to the slide.

The reagent strip 10 may be produced by molding a polyethylene strip with chambers separated by various preselected distances, and therefore producing the reagent timing of the assay to be performed. The reagent capsules are then inserted into the molded spaces or chambers, and a rigid plastic strip may be welded to the surface of the molded strip. Finally, a tubing connection is sealed or connected to the end of the molded channel or common passageway 16. A reusable slide holder, with a length of tubing may be connected to the attachment at the end of the common passageway 16. The slide holder may contain two slides facing each other, clamped into place to form a space there between where the reagents may act on the cellular or other biological material. The reagent is fed into the space between the slides which is slightly larger than that required for capillary action or draw, and therefore relies on positive pressure created by the roller or other pressing means moving down the reagent strip. The reagents fill into space 24 between the slides against the force of gravity, allowing an even filling of the space, and good contact between the reagents and the cellular or other biological material.

This reagent strip technology may be used for standard histochemical slide staining, complex timed immunohistochemical chemical procedures, and with the addition of a thermal controlled slide holder, an automated in-situ hybridization technique.

In operation, upon a chamber 20 being compressed, capsule 22 bursts allowing a reagent to pass under positive pressure through passageway 16 and chamber 14 and to be fed into double slide 12 against the force of gravity, that is an upward direction to fill space 24. Outlet or vent 26 is provided to allow air to escape and to allow overflow of material into a waste receptacle. The waste receptacle may be provided with a disinfectant to neutralize any potentially biohazardous material shed from the slide based specimen. Spacer 32 of double slide 12, as shown in greater detail in FIG. 4, is selected to be of a thickness such that capillary action is not involved. Instead the positive pressure of the roller moves the reagents, which fill the space 24 in a controlled manner, allowing complete coverage of reagents on the portion of the slides which contain the cellular or other biological material 34. The outlet 26 releases waste to a waste container which may contain a disinfectant as described above. This configuration allows for a sealed system in which no human contact with the biological material is necessary. Furthermore, any hazardous chemical reagents are sealed within the closed system, eliminating human contact.

Referring now to FIGS. 5 and 6, there is shown a structure for providing pressure or a pressing apparatus 40 for applying pressure to reagent strip 10. Pressing apparatus 40 may include a housing 42 which may have a recess or other place for receiving reagent strip 10 such as between guides 44. Reagent strip 10 may merely abut guides 44 or may insert within a recess in guides 44. A projection 46 may project through index opening 18 on reagent strip 10 for indexing the strip at an appropriate starting position. As discussed above with respect to indexing opening 18, the indexing projection 46 may take various other suitable forms including projections from guides 44 which would mate with indentations in the side of the reagent strip or various other suitable indexing arrangements. The pressing apparatus 42 is provided with a roller 48 which is moved along reagent strip 10 in the direction of arrow 50 to sequentially compress chambers 20 and capsules 22 to release reagents in a predetermined sequence and timing. Roller 48 may preferably be mounted in a yoke 52 which is spring loaded against substantially U shaped frame 56 by means of spring 54.

As shown in FIG. 6, frame 56 may be moved in the direction of arrow 50 by means of a small electric motor 60 which rotates a threaded shaft 62 on which a threaded hook 58 of frame 56 rides. Other means may be utilized to move frame 56 in the direction of arrow 50 however, in the presently preferred embodiment, an elongated threaded hook 58 would ride on shaft 62. Hook 58 is elongated to provide stability. An area 64 adjacent motor 60 may be unthreaded so that the frame 56 automatically stops without the need for microswitches and the like. However, it will be apparent to those skilled in the art that various other arrangements are possible within the scope and spirit of the invention including the suggested use of a microswitch to stop the motor. Motor 62 may preferably be a small DC motor, but other suitable motors may be utilized. In the presently preferred embodiment, threaded hook 58 and its integral frame 56 may be released from threaded shaft 62 and slid in a direction opposite to arrow 50 to its starting position by depressing frame 56 downardly against spring 54. Applicant presently contemplates as a preferred embodiment an uncomplicated and relatively inexpensive structure for providing the pressing action necessary to release the reagents from the reagent strip 10. However, it is understood that various other arrangements of providing a pressing structure may be utilized.

One other suitable arrangement for providing a pressing structure is shown in FIG. 7 wherein reagent strip 10 would be fed through a pair of rotating rollers 66 and 68. Roller 66 and 68 would operate at a constant speed and be driven by a suitable motor and or motor gear arrangement. Alternatively, rollers 66 and 68 may not be driven, but the reagent strip 10 may be fed into rollers 66 and 68, which may freely rotate, by an apparatus which feeds the strip 10 into the rollers at a constant rate of speed. A light source and a cooperating photocell could be utilized, for example, to detect index opening 18 or other suitable arrangements for indexing could be provided within the spirit of the present invention. Furthermore, indexing is not always required, as the critical timing steps are often between the applications of the reagent and the sequence of the reagents, rather than any precise starting time.

In summary, this invention utilizes a reagent strip approach to contain the reagents necessary for a cytochemical or immunocytochemical procedure in a flexible reagent strip, which is in turn connected to a space formed between two slides (a double slide) arranged face to face and separated by a relatively thick gasket or spacer 32. This allows the application of reagents to the space in which the biological material is contained on one of the slides with positive pressure, not by capillary action. In a presently preferred embodiment, spacer 32 is approximately 1 mm thick.

Further, each reagent is isolated and sealed in a thin plastic capsule of polyethylene or other suitable plastic material. A continuous rate rolling mechanism or other pressing mechanism is used to break the reagent capsule and advance the reagent down a reagent or common passageway 16 which is preferably molded into the reagent strip, and to the space formed between the double slide (two slides with a spacer there between wherein the biological material to be acted on by the reagents is provided on one of the slides). The reagents may exit the space between the slides through an outlet or vent to a waste container.

Incubation times may be programmed into the strip by leaving gaps or spaces between the chambers containing the reagent capsules. The longer the gap, the longer the incubation time. Since all of the reagents and incubations times are contained on the reagent strip, the entire procedure is in essence pre-programmed at the manufacturer. This allows for a significant amount of control of how a set of reagents may be used and simplifies customer support. The greater the control that is exerted over the cytochemical or immunohistochemical process, the greater the reproducibility and accuracy of that procedure.

In view of the above, the present invention may be embodied in other specific forms without departing from the spirit or essential attributes thereof and, accordingly, reference should be made to the appended claims, rather than to the foregoing specification as indicating the scope of the invention.

I claim:

1. A reagent strip slide treating apparatus, comprising:

a reagent strip, said reagent strip comprising a plurality of chambers and a reagent passageway, said reagent passageway connecting to each of said chambers and connecting to a common passageway, said plurality of chambers being arranged at variable predetermined distances along said strip;

a double slide having a first and a second slide spaced apart by a predetermined distance and adapted to have there-between a biological material to be treated sequentially by a plurality of reagents;

a tube connecting said common passageway of said strip to the space between said spaced slides;

a plurality of capsules containing reagents within said chambers, said capsules having walls adapted to burst upon the application of pressure; and structure for providing pressure to said reagent strip sufficient to compress said chambers and burst said capsules in said chambers, said pressure being applied at a uniform rate of speed along a predetermined length of said strip.

2. A reagent strip slide treating apparatus in accordance with claim 1 wherein said reagent strip is comprised of molded polyethylene.

3. A reagent strip slide treating apparatus in accordance with claim 1 wherein said space between said spaced apart slides is selected to be of a predetermined distance such that reagent is not drawn into said space by capillary action.

4. A reagent strip slide treating apparatus in accordance with claim 1 wherein said reagent strip is provided with a means for indexing said reagent strip on the structure for providing pressure.

5. A reagent strip slide treating apparatus in accordance with claim 1 wherein said structure for providing pressure is an apparatus which include a support for said reagent strip, and a roller adapted to be driven over said strip by a constant speed motor.

6. A reagent strip slide treating apparatus in accordance with claim 5 wherein said roller is driven by said motor by means of a threaded member which is moved along a rotating threaded shaft.

7. A reagent strip slide treating apparatus in accordance with claim 1 wherein said structure for providing pressure comprises a pair of rotating rollers operating at a constant speed.

8. A reagent strip slide treating apparatus in accordance with claim 1 wherein said reagent strip includes at least two chambers substantially side by side such that reagent containing capsules may be burst substantially simultaneously for mixing immediately prior to delivery through said tube to said double slide.

9. A reagent strip slide treating apparatus, comprising:

a reagent strip, said reagent strip comprising a plurality of chambers and a reagent passageway, said reagent passageway connecting to each of said chambers and connecting to a common passageway, said plurality of chambers being arranged at variable predetermined distances along said strip;

a plurality of capsules containing reagents, one of said capsules being contained within at least selected ones of said plurality of chambers, said capsules having walls adapted to burst upon application of pressure;

structure for providing pressure to said reagent strip and said capsules in said chambers, said pressure being applied at a uniform rate of speed along a predetermined length of said strip whereby reagent may be squeezed out of said capsules in said chambers into said common passageway in a predetermined sequence and at variable predetermined intervals as determined by said variable predetermined distances;

means adapted for supplying reagent from said common passageway to biological material contained on a microscope slide; and said microscope slide being provided with a structure for forming an enclosed space in which said biological material is present and in which said reagent may treat said biological material, said space being formed by a second microscope slide spaced from said microscope slide by a gasket having an opening therein, said gasket being selected to have a predetermined thickness sufficient to prevent capillary draw into said space.

10. A reagent strip slide treating apparatus in accordance with claim 9 wherein pressure is provided to said strip by means of a roller driven over said reagent strip at a constant rate of speed.

11. A reagent strip slide treating apparatus in accordance with claim 9 wherein said reagent strip slide is fed into a narrow opening at a constant rate of speed thereby causing said capsule containing chambers to be compressed sequentially.

* * * * *